(12) United States Patent
Vakharia et al.

(10) Patent No.: US 10,792,354 B2
(45) Date of Patent: Oct. 6, 2020

(54) FEED ADDITIVE COMPOSITION FOR IMMUNOPROTECTION OF FISH AGAINST INFECTIOUS VIRAL SPECIES

(71) Applicants: University of Maryland Baltimore County, Baltimore, MD (US); Allotropic Tech, LLC, Baltimore, MD (US)

(72) Inventors: Vikram N. Vakharia, Bowie, MD (US); Robert Balcerzak, Baltimore, MD (US)

(73) Assignees: UNIVERSITY OF MARYLAND BALTIMORE COUNTY, Baltimore, MD (US); ALLOTROPIC TECH, LLC, Baltimore, MD (US)

( * ) Notice: Subject to any disclaimer, the term of this patent is extended or adjusted under 35 U.S.C. 154(b) by 0 days.

(21) Appl. No.: 16/237,325

(22) Filed: Dec. 31, 2018

(65) Prior Publication Data
US 2019/0201518 A1    Jul. 4, 2019

Related U.S. Application Data (60) Provisional application No. 62/612,553, filed on Dec. 31, 2017.

(51) Int. Cl.
*A61K 39/12*    (2006.01)
*A61K 39/39*    (2006.01)
(Continued)

(52) U.S. Cl.
CPC ............ *A61K 39/12* (2013.01); *A61K 9/0053* (2013.01); *A61K 9/0056* (2013.01); *A61K 9/113* (2013.01);
(Continued)

(58) Field of Classification Search
None
See application file for complete search history.

(56) References Cited

U.S. PATENT DOCUMENTS 6,936,256 B2 * 8/2005 Vakharia ................ A61K 39/12
424/204.1
9,500,653 B2 11/2016 Crews et al.
(Continued)

FOREIGN PATENT DOCUMENTS

EP    1420819 B1    5/2008

OTHER PUBLICATIONS

Wi et al. Protective immunity against nervous necrosis virus in convict grouper Epinephelus septemfasciatus following vaccination with virus-like particles produced in yeast Saccharomyces cerevisiae. Vet Microbiol. May 15, 2015;177(1-2):214-8. (Year: 2015).*
(Continued)

*Primary Examiner* — Michelle S Horning
(74) *Attorney, Agent, or Firm* — Hultquist, PLLC; Steven J. Hultquist (57) ABSTRACT

An oral vaccine composition for fish, and related oral vaccine delivery system and methods for making and using such oral vaccine composition and delivery system are described. The oral vaccine composition includes virus-like particles effective to mediate an immunoprotective response in a target fish species, wherein the virus-like particles are contained in biomass of an organism or cell culture in which the virus-like particles have been expressed, optionally further including (i) adjuvant effective to enhance the immunoprotective response of the virus-like particles in the target fish species; (ii) encapsulant protectively associated with the virus-like particles for selective locus bioavailability in the target fish species; and/or (iii) binding agent aggregating the ingredients of the composition with one another.

20 Claims, 3 Drawing Sheets
(2 of 3 Drawing Sheet(s) Filed in Color)
Specification includes a Sequence Listing.

(51) Int. Cl.
*A61K 9/00* (2006.01)
*A61K 9/70* (2006.01)
*A61K 9/14* (2006.01)
*A61P 31/12* (2006.01)
*A61K 9/113* (2006.01)
*A61K 39/00* (2006.01)
*A61K 47/38* (2006.01)
*A61K 47/44* (2017.01)

(52) U.S. Cl.
CPC .................. *A61K 9/14* (2013.01); *A61K 9/70* (2013.01); *A61K 39/39* (2013.01); *A61P 31/12* (2018.01); *A61K 47/38* (2013.01); *A61K 47/44* (2013.01); *A61K 2039/5258* (2013.01); *A61K 2039/542* (2013.01); *A61K 2039/552* (2013.01)

(56) References Cited

U.S. PATENT DOCUMENTS

| | | |
|---|---|---|
| 9,538,734 B2 | 1/2017 | Peterson |
| 2008/0286294 A1 | 11/2008 | Thiery et al. |
| 2012/0040010 A1* | 2/2012 | Harel .................. A61K 9/0043 424/499 |

OTHER PUBLICATIONS

Xue et al. Oral vaccination of BacFish-vp6 against grass carp reovirus evoking antibody response in grass carp. Fish & Shellfish Immunology Volume 34, Issue 1, Jan. 2013, pp. 348-355 (Year: 2013).*

* cited by examiner

FEED ADDITIVE COMPOSITION FOR IMMUNOPROTECTION OF FISH AGAINST INFECTIOUS VIRAL SPECIES

CROSS-REFERENCE TO RELATED APPLICATION

The benefit under 35 USC § 119 of U.S. Provisional Patent Application 62/612,553 filed in the United States Patent and Trademark Office on Dec. 31, 2017 is hereby claimed. The disclosure of such U.S. Provisional Patent Application 62/612,553 is hereby incorporated herein by reference in its entirety, for all purposes.

FIELD

The present disclosure relates to oral vaccine compositions for fish and to delivery systems and related methods of making and using such compositions and delivery systems.

DESCRIPTION OF THE RELATED ART

Aquaculture currently provides over half of the 160 million tons of seafood is harvested each year, and continues to grow rapidly. Disease is the primary economic threat to the industry, and is the focus of intensive worldwide efforts to combat a wide spectrum of pathogenic threats. Viral disease threats are particularly problematic. As an illustrative example, virulent infectious pancreatic necrosis virus (IPNV) strains of Sp and A1 serotypes affect Atlantic and Pacific Salmon and Rainbow Trout worldwide. As another example, nervous necrosis virus (NNV), the causative agent of "viral nervous necrosis" (VNN), is infectious to over 30 fish species worldwide, including European sea bass, groupers, red drum, tilapia, Asian sea bass, and barramundi, and has a mortality rate of 80-100% in larval and juvenile fish, and no available commercial treatment.

In the effort to combat viral diseases in aquaculture fish species, the use of injected vaccines introduces significant difficulties in achieving inoculation of large fish stock populations in an accessible, inexpensive, and efficient manner.

In consequence, the art continues to seek improvements in delivery of vaccines to target fish species to generate immunoprotective responses against viral infections, particularly virulent viral infections such as IPNV and NNV.

SUMMARY

The present disclosure relates to oral vaccine compositions for fish and to delivery systems and related methods of making and using such compositions and delivery systems.

In one aspect, the disclosure relates to an oral vaccine composition comprising virus-like particles effective to mediate an immunoprotective response in a target fish species, wherein the virus-like particles are contained in biomass of an organism or cell culture in which the virus-like particles have been expressed.

Such oral vaccine composition may further comprise one or more ingredients selected from the group consisting of: (i) adjuvant effective to enhance the immunoprotective response of the virus-like particles in the target fish species; (ii) encapsulant protectively associated with the virus-like particles for selective locus bioavailability in the target fish species; (iii) binding agent aggregating the virus-like particles and other ingredient(s) of the composition with one another, and (iv) ingredients having two or more functional characteristics of the ingredients (i), (ii), and (iii).

In a further aspect, the disclosure relates to an oral vaccine composition comprising virus-like particles effective to mediate an immunoprotective response in a target fish species, wherein the virus-like particles are contained in biomass of an organism or cell culture in which the virus-like particles have been expressed, and the biomass is contained in the oral vaccine composition in a powder form, wherein the powder form biomass is encapsulated in oil or cellulose based matrices.

In another aspect, the disclosure relates to a delivery system comprising the oral vaccine composition as variously described herein.

In a further aspect, the disclosure relates to a method of manufacturing the oral vaccine composition as variously described herein, such method comprising: (i) generating the virus-like particles by expression thereof from a nucleotide expression construct constituted for such expression, in a host organism or cell culture transformed with such nucleotide expression construct; (ii) converting the host organism or cell culture transformed with the nucleotide expression construct, wherein the virus-like particles have been expressed, to a corresponding biomass; and (iii) recovering the biomass containing the virus-like particles, and optionally formulating the biomass containing the virus-like particles in a powder form with at least one ingredient with at least one of adjuvant, encapsulant, and binding character, to produce the oral vaccine composition.

A further aspect of the disclosure relates to a method of inoculating a fish or fish population against viral disease, comprising applying the oral vaccine composition as variously described herein to an aqueous medium containing or thereafter to contain the fish or fish population, and mediating ingestion by the fish or fish population of the applied oral vaccine composition.

The disclosure in yet another aspect relates to a method of inoculating a fish or fish population against viral disease, comprising orally administering to the fish or fish population effective amount of an oral vaccine composition as variously described herein, and thereafter administering to the fish or fish population a booster inoculation of the first applied oral vaccine composition or by injection of virus-like particles (VLPs) of a same type as contained in the oral vaccine composition.

Other aspects, features and embodiments of the disclosure will be more fully apparent from the ensuing description and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The present disclosure relates to oral vaccine compositions for generating immunoprotective response in target fish species, and to delivery systems and methods of making and using such compositions and delivery systems.

As used herein and in the appended claims, the singular forms "a", "and", and "the" include plural referents unless the context clearly dictates otherwise.

As used herein and in the appended claims, the terms "virus-like particles" or "VLPs" refer to particles comprising outer capsid proteins without the genomic material of a virus, which mimic natural configurations of authentic virions and elicit both humoral and cell-mediated immune responses, but which are non-replicative in character. The term "virus-like particles" is intended to be broadly construed herein to encompass sub-viral particles comprising viral structural proteins which are immunogenic and effective as a subunit vaccine.

The disclosure relates in one aspect to an oral vaccine composition comprising virus-like particles effective to mediate an immunoprotective response in a target fish species, wherein the virus-like particles are contained in biomass of an organism or cell culture in which the virus-like particles have been expressed. The biomass may be produced from the organism or cell culture by any suitable techniques, including for example, lyophilization or freeze-drying, dehydration, desiccation, pulverization, irradiation, or treatment with virucide that yields the biomass in a safe and biocompatible form. The physical form of the biomass may be of any suitable character adapted for utilization in the oral vaccine composition, e.g., a flake, pellet, particle, granule, powder, tablet, or other physical form, as may result from the biomass production method that is used, or as resulting from specific biomass processing techniques or operations. Preferably, the physical form of the biomass is a powder, which has been found particularly useful in formulation of the oral vaccine composition.

The oral vaccine composition may further comprise one or more ingredients selected from the group consisting of: (i) adjuvant effective to enhance the immunoprotective response of the virus-like particles in the target fish species; (ii) encapsulant protectively associated with the virus-like particles for selective locus bioavailability in the target fish species; (iii) binding agent aggregating the virus-like particles and other ingredient(s) of the composition with one another, and (iv) ingredients having two or more functional characteristics of the ingredients (i), (ii), and (iii). For example, the composition may include an adjuvant that is effective as a coating on feed pellets, as well as being an effective binder for the oral vaccine composition. Alternatively, the composition may contain only an adjuvant, or only an encapsulant, or only a binding agent, or it may contain two or all three of such types of ingredients.

In a further aspect, the disclosure relates to an oral vaccine composition comprising virus-like particles effective to mediate an immunoprotective response in a target fish species, wherein the virus-like particles are contained in biomass of an organism or cell culture in which the virus-like particles have been expressed, and the biomass is contained in the oral vaccine composition in a powder form, wherein the powder form biomass is encapsulated in oil or cellulose matrices. The oil of the oil matrix may be of any suitable type and may for example comprise soy oil, canola oil, grape seed oil, coconut oil, or any other appropriate biocompatible oil serving to encapsulate the powder form biomass and rendering the VLPs therein bioavailable to the fish to which it is administered. The cellulose of the cellulose matrix may be of any suitable type and may be for example ethyl cellulose, serving to encapsulate the powder form biomass, protecting the VLPs in acidic environment, and rendering the VLPs therein bioavailable in the hindgut of fish when it is administered.

The biomass when provided in a powder form may be derived from an insect or other organism in which the VLPs have been expressed subsequent to transformation of the organism with a suitable recombinant vector constituted for expression of the VLPs with accompanying genomic material for forming VLPs of the corresponding virus being present in the vector. Preferably, the vector is a baculovirus vector, although any of numerous other vectors could be advantageously employed.

The oral vaccine composition may contain, in addition to the virus-like particles in an organism-derived or culture-derived biomass, any additional ingredient(s) such as those illustratively described above (e.g., adjuvants, encapsulants, binders, etc.) in any suitable amounts and relative proportions to one another. In various specific embodiments, the amount of the virus-specific proteins in the oral vaccine composition is in a range of from 0.05 mg to 0.15 mg in the corresponding dose form of the composition, such as a pellet, tablet, or other unitary dose form.

The binding agent aggregating the virus-like particles, adjuvant, and/or encapsulant with one another may also be of any suitable type, and may for example comprise a polysaccharide such as starch, a biodegradable and biocompatible organic resin, or other suitable material that effects the aggregation of the various vaccine composition ingredients with one another.

The oral vaccine composition may also contain any of various suitable excipients, including antioxidants, stabilizers, preservatives, formulation aids, etc.

The oral vaccine composition may be utilized in any suitable form, as discussed above, and may for example be applied as a coating on feed pellets, e.g., to provide an amount of the oral vaccine composition thereon in a range from 1 to 5% by weight, based on weight of the feed pellets.

The vaccine composition once formulated may be shaped or formed into appropriate dose forms for administration, e.g., by tableting, pelletizing, granulating, or other operations. The vaccine composition during such product formation may be subjected to further processing, such as exposure to gamma radiation or other sterilant media or conditions to ensure the absence of any replicatively competent genomic material in the final product.

In various embodiments, the virus-like particles utilized in the oral vaccine composition of the present disclosure may be generated in situ by transfecting, into a recipient organism such as for example an insect, or into a cell culture, viral vectors that are constituted to express the structural proteins of the virus-like particles in the recipient organism or cell culture. The transformed organism or cell culture containing the virus-like particles may subsequently be processed, e.g., by lyophilization, ambient desiccation, flash freezing, or other suitable process technique, to provide a VLP-containing biomass as an ingredient for the oral vaccine composition. Examples of suitable organisms for such processing include artemia nauplii, copepods, and rotifers, but may otherwise include any of a wide variety of advantageous organisms. Insects such as crickets and grasshoppers may also be used as transformable species for expression of the VLPs from a suitable vector, and subsequent to transfection and expression, such insects may be processed into meal or flour for use in the oral vaccine composition.

As a specific example of production of VLP-containing biomass for use in the oral vaccine composition of the present disclosure, a baculovirus system may be constituted as a recombinant vector derived from *Autographa californica* multiple nucleopolyhedrovirus (AcMNPV) for expression of target structural proteins of the VLP of a selected virus, such as IPNV, NNV, etc. Such baculovirus vector may be used to orally infect an organism such as an insect, e.g., *Trichoplusia ni* larvae, which subsequent to transfection and expression of the VLPs may be lyophilized to provide an insect larvae biomass that is subjected to granulation to form a corresponding biomass powder, or the larvae may otherwise be processed into an edible form, as a VLP-containing ingredient of the oral vaccine composition.

As alluded to above, the oral vaccine composition once formulated can be shaped or processed into a form for fish consumption. For example, the oral vaccine composition may be pelletized or otherwise formed into multiple discrete bodies as a dose form for the vaccine. Alternatively, the oral vaccine composition may be top coated on granules, grains, or other particles of food to be fed to the fish to be inoculated, thereby providing a vaccine-augmented food material for ingestion by the target fish species. To top-dress the vaccine composition on a feed material, a coating agent is usually applied, e.g., canola oil, to prevent leaching of the antigen from the composition or to prevent break-down of the antigen in the acidic pH environment of the fish stomach.

The oral vaccine composition in a form for fish consumption may then be dosed orally during normal feeding cycles of the target fish species. The oral vaccine dose form may be administered to the surface of the water in a tank or otherwise dispersed in the water so that the oral vaccine dose form is made available for ingestion by the fish in the tank, e.g., to produce a mucosal immunoprotective response in the fish.

Such administration of the oral dose form of the vaccine composition may be carried out at any appropriate stage of the fish development and in accordance with any suitable dosing schedule to provide effective inoculation of the fish. For example, the oral vaccine dose form may be administered to the fish at the fry stage, with a once-only administration or alternatively a repeated administration to a given fish population, as appropriate to confer the desired immunity to the specific fish population.

The oral vaccine composition of the present disclosure in various embodiments may comprise the antigenic VLPs in freeze-dried larvae powder of insect larvae in which the VLPs have been expressed. The antigenic VLPs in the freeze-dried larvae powder may be microencapsulated by coating the powder with an oil-based matrix material such as soy oil or other suitable oil-based matrix material or ethyl cellulose matrix. Such coating of the powder with the soy oil or ethyl cellulose will protect the VLP proteins from the harsh environment of the fish stomach and slowly release the VLP proteins at the desired hindgut site.

In specific embodiments, the organism in which the antigenic VLPs have been expressed may be cabbage loopers (*Trichoplusia ni*) or crickets which are then processed to form insect flour containing the VLPs. Such insect flour may be microencapsulated with fully hydrogenated soy oil or ethyl cellulose for the functional purpose of effecting delayed-release in fish species to which the oral vaccine composition comprising such microencapsulated insect flour is fed. The fully hydrogenated soy oil or ethyl cellulose may be applied to the insect flour by spraying, fluidized bed contacting, or any other of various techniques by which the oil or cellulose may be aggregated with the insect flour to microencapsulate it.

The microencapsulated insect flour may have a mottled dark tan to brick red color, as a free-flowing granular powder having a loose bulk density on the order of about 0.40 g/cc and a particle size distribution allowing 100% passage of the powder through a US Standard #14 mesh sieve. Such an oral vaccine composition can be stored at 20° C. and 50% relative humidity with an expected shelf life of 24 months, rendering it storage-capable at aquaculture facilities as a vaccine resource of such facilities.

A variety of types of adjuvant may be utilized in the oral vaccine composition of the present disclosure. The adjuvant may function in the oral vaccine composition, in addition to its adjuvant functionality of enhancing the immune response, as an encapsulant and/or a binder for the oral vaccine composition. By way of specific example, a liquid oil adjuvant may be employed such as Essai GR01PR, an adjuvant commercially available from Seppic S.A., Paris, France that contains a gastro-resistant matrix allows formulation of the oral vaccine composition by mixing the adjuvant in aqueous medium to form an emulsion which then is applied to the VLP-containing biomass particles, by spraying, food bed contacting, or other suitable application technique, to yield adjuvant-coated VLP-containing biomass particles that are then suitable for dispersion on or in a water medium containing the fish to be vaccinated, to enable the ingestion of same by the fish.

The Essai GR01PR adjuvant may be formulated with aqueous medium at a suitable relative amounts ratio, e.g., 70 weight percent adjuvant: 30 weight percent aqueous medium, with the mixture then being emulsified under high shear processing conditions. In an illustrative procedure, the adjuvant may be placed in an appropriate container, following which agitation may be initiated, e.g., at a rotational mixer speed of 1500 RPM, and aqueous phase may be slowly added into the adjuvant, while agitation speed is increased to 4000 RPM for a suitable period of time, e.g., 3-5 minutes, to form the emulsified adjuvant component which may then as previously mentioned be sprayed or otherwise applied to the VLP-containing biomass particles. The resulting adjuvant-coated VLP-containing biomass particles will retain the adjuvant coating on the biomass particles after immersion, e.g., for up to 10-12 hours.

The VLPs that are expressed in the organisms subsequently processed to provide corresponding organism-derived biomass containing the expressed VLPs may be of any suitable type, in which the expression derives from a suitable transfection construct that is constituted to avoid any disease causation in the recipient organism. By way of example, the transfection construct may comprise a recombinant baculovirus vector that is administered to the host organism to effect expression of the VLPs in such organism, as a source of subsequently produced organism-derived biomass. Thus, in a specific implementation, a recombinant baculovirus may be employed that expresses the NNV capsid protein that will form VLPs and evoke protective immunity in fish fed with larvae-derived vaccine by oral route. Other host organisms, e.g., silkworms, may be employed, with other appropriate transfection vectors.

The production of baculovirus-infected insect larvae is highly scalable to produce large quantities of the insect larvae, which then can be homogenized, inactivated, lyophilized, and utilized as a feed composition or feed component to vaccinate fish. The recombinant baculovirus may be constituted to express the NNV capsid protein (SEQ ID NO: 1) for generation of the NNV-VLPs in the host organism:

```
Amino acid Sequence of Nervous Necrosis virus
Capsid Protein (338 aas)
                                          (SEQ ID NO: 1)
MVRKGDKKLAKPATTKAANPQPRRRANNRRRSNRTDAPVSKASTVTGFGR

GTNDVHLSGMSRISQAVLPAGTGTDGYVVVDATIVPDLLPRLGHAARIFQ

RYAVETLEFEIQPMCPANTGGGYVAGFLPDPTDNDHTFDALQATRGAVVA

KWWESRTVRPQYTRTLLWTSSGKEQRLTSPGRLILLCVGNNTDVVNVSVL

CRWSVRLSVPSLETPEETTAPIMTQGSLYNDSLSTNDFKSILLGSTPLDI

APDGAVFQLDRPLSIDYSLGTGDVDRAVYWHLKKFAGNAGTPAGWFRWGI

WDNFNKTFTDGVAYYSDEQPRQILLPVGTVCTRVDSEN
```

As another example, IPNV structural proteins may be expressed in a baculovirus/insect cell or insect larvae system resulting in the formation VLPs that are highly immunogenic and effective as a subunit vaccine. VLPs of NNV may also be produced in insect cells or insect cell cultures, e.g., Sf-9 or Sf-21 insect cells.

Figure 1A:
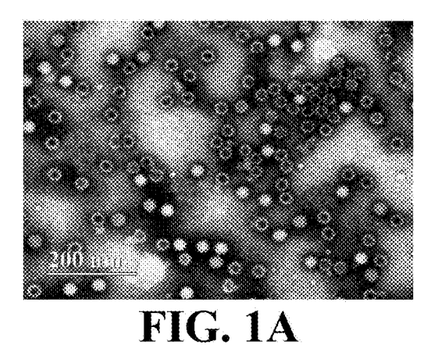
FIG. 1A shows CsCl purified NNV-VLPs, negatively stained with Na-phosphotungstate. Bar=200 nm.
Figure 1B:
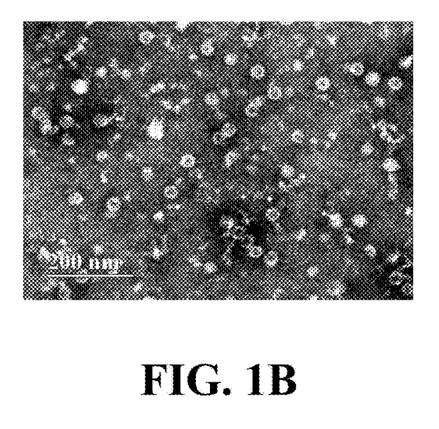
FIG. 1B is an electron micrograph image of CsCl purified nervous necrosis virus.

FIG. 1A shows the presence of baculovirus-expressed NNV-VLPs of about 33 nm in size, which is identical to the native NNV shown in FIG. 1B. FIG. 1A shows CsCl purified NNV-VLPs, negatively stained with Na-phosphotungstate. Bar=200 nm. FIG. 1B is an electron micrograph image of CsCl purified nervous necrosis virus.

The disclosure in another aspect relates to a delivery system comprising the oral vaccine composition as variously described herein. Such delivery system may include the oral vaccine composition formulated as a coating material, and the delivery system may comprise a feed material on which the oral vaccine composition coating material is coated. The delivery system may comprise the oral vaccine composition in a tableted, pelletized, or granular dose form.

A further aspect of the disclosure relates to a method of manufacturing the oral vaccine composition as variously described herein, such method comprising: (i) generating the virus-like particles by expression thereof from a nucleotide expression construct constituted for such expression, in a host organism or cell culture transformed with such nucleotide expression construct; (ii) converting the host organism or cell culture transformed with the nucleotide expression construct, wherein the virus-like particles have been expressed, to a corresponding biomass; and (iii) recovering the biomass containing the virus-like particles, and optionally formulating the biomass containing the virus-like particles in a powder form with at least one ingredient with at least one of adjuvant, encapsulant, and binding character, to produce the oral vaccine composition.

The VLP-containing biomass may be processed to provide a coating formulation that is coated on feed pellets. Alternatively, the VLP-containing biomass may be mixed with a feed composition, and the resulting mixture may then be pelletized to provide composite feed pellets. Any other processing methods suitable to form a VLP-containing biomass-incorporated product may be employed.

The above-discussed manufacturing methods may further comprise sterilizing the oral vaccine composition, e.g., by irradiation with gamma radiation, UV radiation, X-rays, or other radiation, or by exposure to a sterilant gas or other sterilizing medium.

The quality assurance operations associated with the production of the oral vaccine composition of the present disclosure may include assays or tests for determination that the viral vector used for inducing expression of VLPs in the host organism or host cell culture has been rendered inactive in the resulting biomass. This may include testing the host organism or host cell culture with lyophilized, irradiated material to confirm that it fails to produce virus-specific infection or cytopathic effect, respectively, indicating that any infectious virus present in the biomass has been rendered inactive.

A further aspect of the disclosure relates to a method of inoculating a fish or fish population against viral disease, comprising applying the oral vaccine composition as variously described herein to an aqueous medium containing or thereafter to contain the fish or fish population, and mediating ingestion by the fish or fish population of the applied oral vaccine composition, e.g., by allowing ingress of the fish or fish population into a tank to which the oral vaccine composition has been applied to the aqueous medium, or by applying the oral vaccine composition at a scheduled feeding time, or in other mediating manner.

In such method, the virus-like particles of the oral vaccine composition may comprise nervous necrosis virus (NNV) virus-like particles and/or infectious pancreatic necrosis virus (IPNV) virus-like particles, and/or any other antigenic virus-like particles species.

The disclosure in yet another aspect relates to a method of inoculating a fish or fish population against viral disease, comprising orally administering to the fish or fish population effective amount of an oral vaccine composition as variously described herein, and thereafter administering to the fish or fish population a booster inoculation of the first applied oral vaccine composition or by injection of VLPs of a same type as contained in the oral vaccine composition. This sequential administration, by initial oral inoculation followed by booster inoculation, can be usefully employed when the oral inoculation is administered to fish fry at a predetermined small size, e.g., up to 2 g in weight, and wherein the booster inoculation is administered at larger size, e.g., at 10-12 g in weight. Such sequential prime-boost administration provides enhanced longitudinal immunity to the fish, and thereby serves to efficiently protect fish throughout the period of their cultivation.

The advantages and features of the disclosure are further illustrated with reference to the following examples, which are not to be construed as in any way limiting the scope of the disclosure but rather as illustrative of specific embodiments thereof in particular applications thereof.

Example 1

To develop and evaluate the efficacy of a recombinant oral nervous necrosis virus (NNV) vaccine, 3 recombinant baculovirus constructs that produce host-protective outer capsid protein of NNV and the targeting protein (fused or linked with NNV) in insect larvae were prepared and tested.

The original DNA construct harboring the NNV gene forming VLPs was utilized to construct two additional baculoviruses, TNF-NNV and TNF-T2A-NNV, which have His-tags at the C-terminus of NNV. In the first construct, a targeting protein sequence (TNF) of 17-kDa was fused to the coding sequence of NNV (37-kDa), which would produce a fusion protein of 54-kDa. In the second construct, a self-cleaving peptide sequence of 25 amino acids (T2A) was placed in frame between TNF and NNV coding sequence which would give rise to the targeting protein and NNV protein (with His-tag) after cleavage. These DNA constructs were used to generate recombinant baculoviruses, according to the standard protocol described by the manufacturers of various Baculovirus Expression System kits.

Figure 4:
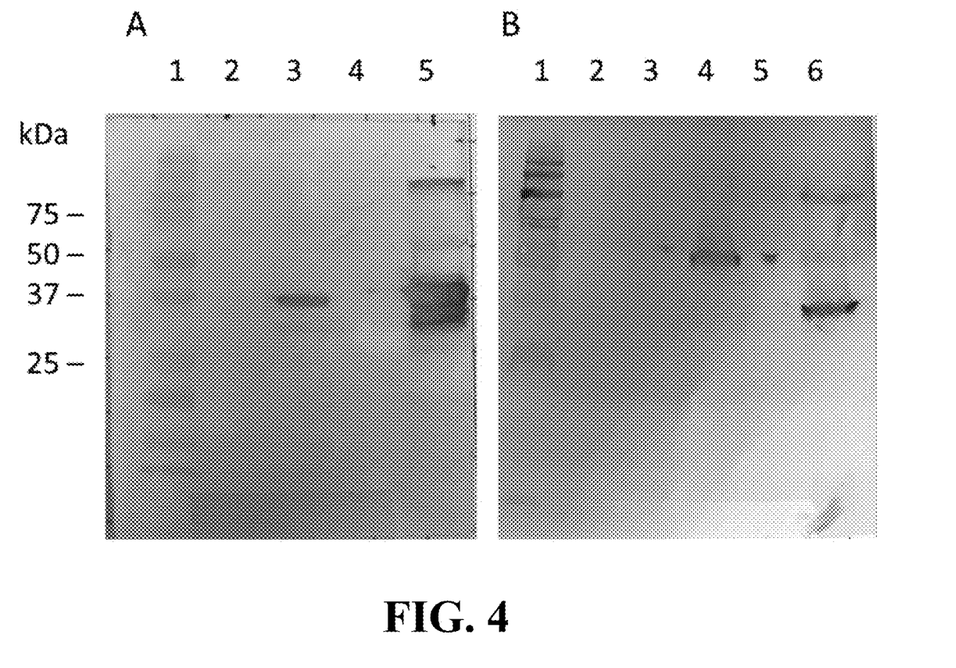
FIG. 4 shows a Western blot analysis of the proteins produced by recombinant baculovirus infected cells.

FIG. 4 shows Western blot analysis of the proteins from baculovirus infected insect or insect larvae cell lysates which were fractionated on a 12.5% SDS-polyacrylamide gel and probed with anti-NNV antibody. Panel A shows pre-stained protein marker from Bio-Rad (Lane 1); mock-infected Sf-9 insect cell lysate (Lane 2); recombinant NNV baculovirus infected insect cells lysate (Lane 3); blank (Lane 4); recombinant NNV baculovirus infected insect larvae lysate showing a band of NNV protein and additional band of 110-kDa, a trimer of NNV (Lane 5). Panel B shows pre-stained protein marker from Bio-Rad (Lane 1); nock-infected Sf-9 insect cell lysate (Lane 2); blank (Lane 3); recombinant TNF-NNV baculovirus infected cell lysate showing a band of 54-kDa fusion protein (Lane 4); blank (Lane 5); recombinant TNF-T2A-NNV baculovirus infected cell lysate showing a band of 37-kDa NNV protein after cleavage of T2A (Lane 6).

A baculovirus recombinant vector derived from *Autographa californica* multiple nucleopolyhedrovirus (Ac-MNPV) was constructed for expression of each of the respective NNV-specific proteins, and *Trichoplusia ni* larvae were infected with such vectors, which subsequently after expression of the respective NNV-specific VLPs were lyophilized to provide a freeze-dried larvae powder containing the respective NNV-specific VLPs.

The concentration of NNV protein in freeze-dried insect larvae powder was determined by taking aliquots from initial production runs using a combination of BCA Protein assay kit (Pierce) and CHEMIDOC™ gel/western blot imaging reagents and CHEMIDOC™ Imaging System (Bio-Rad). First, the His-tagged NNV protein from larvae powder was purified using Ni-NTA chromatography and quantified using BCA protein kit. Then a known amount of this protein was loaded along with other samples on a SDS-PAGE gel, immunostained with specific antibodies and analyzed using a CHEMIDOC™ Imaging System. The results indicated that expression of target proteins ranged from 2.48 g to 11.84 g per 200 g of freeze dried larvae or equivalent to 1.0 kg wet weight.

To test for the presence of baculovirus in protein mass that is rendered inactive, each lot of biomass was processed by first by freeze drying and then grinding into a powder. It was noted that insect larvae lose about 80% of its weight after freeze-drying, and in effect yield approximately 200 g of dry mass from 1.0 kg of insect larvae (wet weight). After processing the biomass, powder was analyzed to confirm that the processing did not affect the target antigen. This powder was further processed by exposing to gamma ray irradiation. The purpose of this irradiation was to inactivate the baculovirus and also to make the powder sterile. Each lot was tested to prove that baculovirus was no longer active by carrying out a bioassay in insect larvae, which failed to infect. Samples of each lot were also tested in insect cell culture. When Sf-9 cells were infected with irradiated material, it failed to infect cells and did not produce any cytopathic effect to indicate virus infection. This results indicated that any infectious baculovirus that was present in the original biomass was rendered inactive.

To determine the protein concentration of NNV-specific protein in larvae powder, 20 mg aliquots of each larvae powder 1023A, 1023D, and 1023E were placed in 1.5-ml Eppendorf tube. One ml of ice-cold phosphate buffered saline, pH 7.4/protease inhibitor cocktail (1:100; Sigma P8849) was added and the suspension was sonicated to make a homogenate. Fifty µl of homogenate was mixed with 50 µl of 2× SDS-sample buffer containing 2-mercaptoethanol. Two-fold dilution was carried out using 1× SDS-PAGE buffer to prepare 1×, 2×, 4×, 8×, and 16× diluted samples for SDS-PAGE and Western Blot analysis. Ten µl of each sample was loaded onto 12% SDS-PAGE gel. Thus, 1×, 2×, 4×, 8× and 16× dilution sample loaded in one well corresponds to 100, 50, 25, 12.5 and 6.25 microgram of larvae powder, respectively. On the same gel, 0.1, 0.05, 0.02 or 0.01 µl of purified NNV2 protein was loaded as a standard. The proteins were fractionated on SDS-PAGE, transferred to nitrocellulose membrane and immunostained using rabbit anti-NNV serum (1:1,000), goat anti-rabbit IgG (H+L)-HRP conjugate (1:1,000) and CLARITY WESTERN ECL™ substrate (Bio-Rad). The blot was analyzed using a CHEMIDOC™ Touch Imaging System and its related software. By comparing the intensity of signals from larvae samples and those from NNV standards, the amount of NNV-specific protein was calculated per 100 g of dry weight larvae powder.

Tabulated below is the net weight of freeze-dried, irradiated powder of 3 baculoviruses obtained from 6 larvae production runs that were utilized for testing. The weight listed below for each sample is combined from 2 runs. The yield of NNV specific protein present per 100 g of larvae powder is listed, as judged by the chemiluminescent assay.

| Virus | Gross wt. | Dry wt. | Label | NNV protein/100 g dry wt. |
|---|---|---|---|---|
| NNV (original VLP) | 443.7 g | 313.5 g | 1023A | 2.32 g (×3.135 = 7.273 g) |
| TNF-NNV | 370.6 g | 248.4 g | 1023D | 5.92 g (×2.484 = 14.705 g) |
| TNF-T2A-NNV | 469.5 g | 339.3 g | 1023E | 1.24 g (×3.393 = 4.207 g) |

To test the efficacy of oral vaccines in European sea bass, three types of products were tested at two different doses. TYP1 construct produced only NNV-VLP protein, whereas the TYP2 construct expressed a targeting protein (TNF-α of European sea bass) that was fused to the NNV coat protein at the N-terminus, and the TYP3 construct produced NNV-VLP protein with a 6× His-tag at the C-terminus. The test included small fish (Sm) and big fish (Bg) receiving 1.5% of top-coating (1×) or 3% of top-coating (2×), except that the Bg group did not receive a booster dose.

All NNV antigens present in the freeze-dried larvae powder were top-coated using fish oil on a commercial diet and fed at specific feeding schedule for 1 g (Sm) and 10 g (Bg) fish, as shown in Table 1.

TABLE 1

Feeding design and oral delivery of vaccine in feed top-coated with respective freeze-dried larvae powder (vaccines) and oil.

| | | Av wt at start (g) Start date | Normal Feeding 1 Wed 16 Nov. 2016 | | 1.06 Primary Treatment Tue Nov. 29, 2016 | | 3.81 Normal Feeding 2 Wed Dec. 14, 2016 | | | |
|---|---|---|---|---|---|---|---|---|---|---|
| Tank | No. Fish | Week Start | 1 | 2 | 3 | 4 | 5 | 6 | 7 | 8 |
| 1 | 240 | Naïve | C | C | C + O | C + O | C | C | C | C |
| 2 | 240 | PosCtrl | C | C | C + O | C + O | C | C | C | C |
| 3 | 120 | SmTYP1 | C | C | C + V + O | C + V + O | C | C | C | C |
| 4 | 120 | SmTYP2 | C | C | C + V + O | C + V + O | C | C | C | C |

TABLE 1-continued

Feeding design and oral delivery of vaccine in feed top-coated with respective freeze-dried larvae powder (vaccines) and oil.

| | | | | | | | | | | | | |
|---|---|---|---|---|---|---|---|---|---|---|---|---|
| 5 | 120 | SmTYP3 | C | | C | C + V + O | C + V + O | C | C | C | C | |
| 6 | 120 | SmTYP1-2X | C | | C | C + V + O | C + V + O | C | C | C | C | |
| 7 | 120 | SmTYP2-2X | C | | C | C + V + O | C + V + O | C | C | C | C | |
| 8 | 120 | SmTYP3-2X | C | | C | C + V + O | C + V + O | C | C | C | C | |
| 9 | 120 | BgTYP1-2X | C | | C | C + O | C + O | C | C | C | C | |
| 10 | 120 | BgTYP2-2x | C | | C | C + O | C + O | C | C | C | C | |
| 11 | 120 | BgTYP3-2X | C | | C | C + O | C + O | C | C | C | C | |
| 12 | 240 | Extra Fish | C | | C | C + O | C + O | C | C | C | C | |

| Av wt at start (g) | 10.74 | | 16.74 | | | 30.9 | |
|---|---|---|---|---|---|---|---|
| Start date | Booster Wed Jan. 11, 2017 | | Normal Feeding 3 Thur Jan. 26, 2017 | | | Challenge Thu Mar. 2, 2017 | |

| Tank | Week Start | 9 | 10 | 11 | 12 | 13 | 14 | 15 | 16 | 17 |
|---|---|---|---|---|---|---|---|---|---|---|
| 1 | Naïve | C + O | C + O | C | C | C | C | C | C | C |
| 2 | PosCtrl | C + O | C + O | C | C | C | C | C | C | C |
| 3 | SmTYP1 | C + V + O | C + V + O | C | C | C | C | C | C | C |
| 4 | SmTYP2 | C + V + O | C + V + O | C | C | C | C | C | C | C |
| 5 | SmTYP3 | C + V + O | C + V + O | C | C | C | C | C | C | C |
| 6 | SmTYP1-2X | C + V + O | C + V + O | C | C | C | C | C | C | C |
| 7 | SmTYP2-2X | C + V + O | C + V + O | C | C | C | C | C | C | C |
| 8 | SmTYP3-2X | C + V + O | C + V + O | C | C | C | C | C | C | C |
| 9 | BgTYP1-2X | C + V + O | C + V + O | C | C | C | C | C | C | C |
| 10 | BgTYP2-2x | C + V + O | C + V + O | C | C | C | C | C | C | C |
| 11 | BgTYP3-2X | C + V + O | C + V + O | C | C | C | C | C | C | C |
| 12 | Extra Fish | C + O | C + O | C | C | C | C | C | C | C |

Sm Small Fish
Bg Big Fish
C Commercial diet
C + O Commercial diet coated with oil
C + V + O Commercial diet coated with respective vaccine + oil Fish were grown to the required sizes in 500 liter tanks. TYP1, TYP2, and TYP3 represent A, D, and E samples respectively with 1.5% coating, and TYP-2X represent 3% coating. Small fish were orally fed with top-coated vaccines for 2 weeks, kept at commercial diet for 4 weeks, and boosted along with the big fish group for 2 weeks. Both big and small fish were kept on commercial diet for 4 weeks prior to challenge. Blood samples were taken from 15 fish of selected groups to evaluate immune response using ELISA.

A challenge with NNV was carried out in triplicate with a subset of the population from each treatment with the known dose of 10^4 TCID/50 fish that gave 60-70-% mortality in a pre-challenge study. At the end of the Normal Feeding 3 period, 20 fish from each of the treatments were tagged and inoculated by intramuscular injection (im) with the appropriate dose of NNV and placed into a tank in the challenge bay. This was repeated three times so that the challenge was carried out in triplicate tanks. This process was carried out in such a way that there were triplicate tanks for the group of fish given the Primary Treatment period (+PosCtrl fish) and triplicate tanks for the group of fish given the vaccines only during the Booster period (+PosCtrl fish). Mortalities was followed on a day to day basis until the end of the challenge so as to be able to assess the efficacy of the various antigen treatments by determining the relative percent survival (RPS), which is determined by using the following equation: RPS=1−[% mortality vaccinates/% mortality controls]*100.

Another three tanks each held 20 of the naive fish (untreated fish), each to represent a control group. After 18 days post challenge, the main challenge was terminated once no mortality of fish was detected for 3 days prior to termination. Tables 2 and 3 below show the final % mortality data referring to the two groups of fish that were challenged. There were no mortalities in the 3 tanks containing naive fish.

TABLE 2

Results of mortality in the main challenge for the treatments involving fish provided twice with the respective products. Letters as superscript signify significant differences. ANOVA value was 0.040.

| | Products provided during Primary Treatment and booster phases | | | | | | |
|---|---|---|---|---|---|---|---|
| Treatment | SmTYP1 - A | SmTYP2 - D | SmTYP3 - E | SmTYP1-2X - A | SmTYP2-2X - D | SmTYP3-2X - E | Positive Control |
| Total % of mortality | $40.00^a$ | $65.00^b$ | $55.00^{ab}$ | $38.33^a$ | $68.33^b$ | $41.67^a$ | $66.70^{ab}$ |
| St.dev. (%) | 8.66 | 15.00 | 8.66 | 2.89 | 20.21 | 11.55 | 10.00 |

TABLE 3

Results of mortality in the main challenge for the
treatments involving fish provided only once with
the respective products. ANOVA value was 0.655.

| Treatment | Products provided during Booster phase only | | | |
| --- | --- | --- | --- | --- |
| | BgTYP1-2X - A | BgTYP2-2X - D | BgTYP3-2X - E | Postitive Control |
| Total % of mortality | 53.33 | 60.00 | 60.00 | 70.00 |
| St. dev. (%) | 2.89 | 25.98 | 5.00 | 17.32 |

The results show that samples SmTYP1-A, SmTYP1-2X-A, and SmTYP3-2X-E gave significant protection against a stiff NNV challenge, with an RPS values of 40.0%, 42.5% and 37.4%, respectively. Only 23.9% RPS was obtained in big fish (10.0 g) vaccinated with a single dose for two weeks period. Fifteen blood samples, taken prior to challenge, were analyzed by ELISA and only five samples showed elevated levels of anti-NNV response in vaccinated fish, which is indicative of protective response from the NNV challenge. The SmTYP2 groups, which did not form VLP, exhibited the highest mortality (over 68%).

These results demonstrate that the NNV-VLP antigens delivered orally are stable and confer fair protection in European sea bass.

Protection values can be optimized by giving the vaccine to fish at an early stage, which is ideally suited for hatcheries where the fish are less than 1.0 g, followed by a booster at 6-8 g.

By emulsifying the antigens with adjuvants and/or micro-encapsulation of antigens that will protect the viral antigens, the efficacy of the oral vaccine is substantially increased.

Example 2

In this example, the efficacy of NNV virus-like particles as an injectable vaccine were evaluated. European sea bass were intraperitoneally injected with 0.1 mL of NNV antigen containing about 50 mg of protein/fish. A total of thirty fish (in triplicate) were vaccinated and a group of thirty fish were sham vaccinated. Following vaccination, the fish were held for 6 weeks at 25° C. to confer sufficient immunity prior to challenge. When sham vaccinated fish were challenged with the NNV, a high percent mortality rate (62%) was observed after 26 days post-challenge, whereas the mortality rate of the vaccinated fish was only 4%, as shown in FIG. 2.

Figure 2:
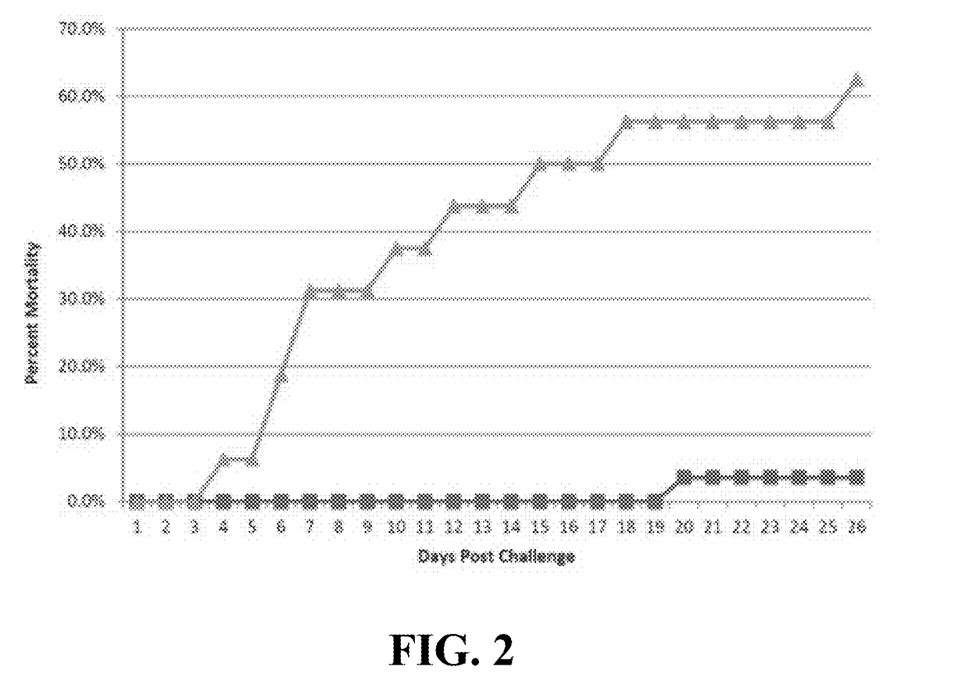
FIG. 2 is a graph of percent mortality as a function of days post challenge, showing the cumulative percent mortality of vaccinated (green) and sham vaccinated (brown) fish after exposure to an NNV challenge dose of $10^5$ TCID50/fish via intra-peritoneal injection.

FIG. 2 is a graph of percent mortality as a function of days post challenge, showing the cumulative percent mortality of vaccinated (green) and sham vaccinated (brown) fish after exposure to an NNV challenge dose of $10^5$ TCID50/fish via intra-peritoneal injection. Mortalities were monitored twice daily and the experiment was terminated when no mortality was observed for 5 days. A representative subset of fish that died during the trial were tested by real-time PCR to determine the presence of NNV.

The results shown in FIG. 2 indicate that NNV-VLP-vaccinated fish were protected, with RPS=94%, suggesting this injectable vaccine is efficacious in protecting European sea bass against NNV infection.

Example 3

This example demonstrates the formation of NNV VLPs and the production of NNV-containing oral vaccine compositions.

To scale-up the production of NNV proteins for injectable vaccine preparations, several batches of T-150 flasks of Sf-21 insect cells were infected with the recombinant baculovirus. Five days post-infection, baculovirus-infected cells were harvested. Approximately, 10-12 g of insect cells were obtained from one liter of culture.

About 42 g of cell pellet, collected from 4 L cultures, was resuspended in 80 ml of 0.01M Tris, pH 8.0, to which 0.6 ml of 10% deoxycholate and 0.03 ml of Benzonase (7500 units) was added. The mixture was incubated on ice for 20 minutes, sonicated 8× for 20 seconds to disrupt the cells, and clarified by centrifugation. The cells were resuspended in 20 ml of Tris buffer and resonicated one more time.

About 25 ml of sonicated material was extracted with 8 ml of Freon (in two tubes), and clarified by centrifugation (Sorvall, 10,000 rpm for 30 min). The upper was pooled into one tube, and the mixture was layered into two ultracentrifuge tubes containing 7 ml of 56% sucrose+15 ml of 28% sucrose, and spun in an ultracentrifuge at 26,000 rpm for 2 hrs, using SW28 rotor. The visible opaque band of NNV-virus-like particles (VLPs) was collected, purified, and analyzed by electron microscope, as shown in FIG. 1.

Figure 3:
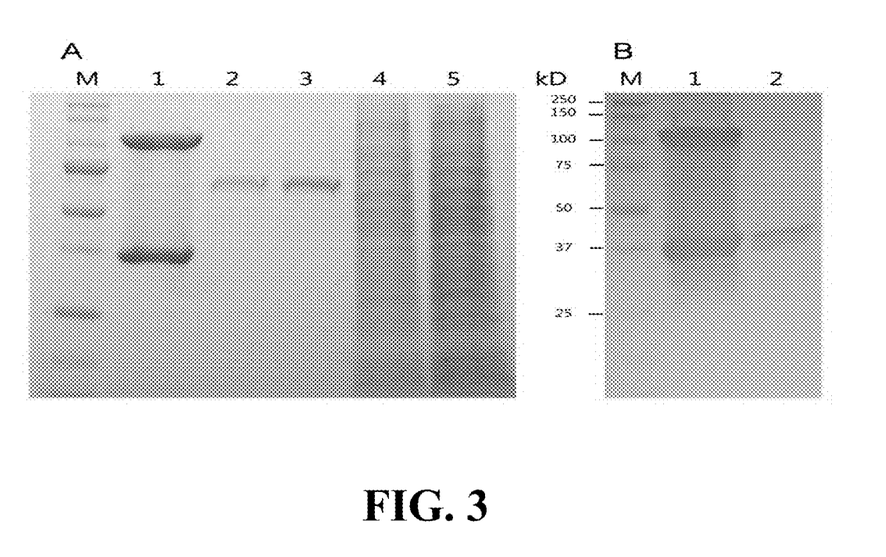
FIG. 3 shows Coomassie Blue staining of the proteins from baculovirus infected cell lysate and CsCl purified NNV-VLPs (Panel A) and Western blot of the same samples, probed with anti-NNV-antibody (Panel B).

A portion of the sample was loaded on a 12.5 SDS-polyacrylamide gel, and the protein was stained by Coomassie blue or immunostained with NNV-specific polyclonal antibody to confirm and quantify the presence of NNV protein, as shown in FIG. 3. The yield of NNV-specific protein was approximately 0.5 mg/ml in sonicated lysate, as judged by BCA Protein assay kit (Pierce).

FIG. 3 shows Coomassie Blue staining of the proteins from baculovirus infected cell lysate and CsCl purified NNV-VLPs (Panel A) and Western blot of the same samples, probed with anti-NNV-antibody (Panel B).

When baculovirus-infected cell lysate was fractionated on a 12.5% SDS-polyacrylamide gel, bands of 37-40-kDa and 110-kDa (trimer) reacted with NNV-specific polyclonal antibody, which co-migrated with CsCl purified NNV-VLPs. Panel A shows pre-stained protein marker from Bio-Rad (Lane: M); 2.5 μl of CsCl purified NNV-VLPs (Lane 2); 1.0 μg and 2.5 μg of purified BSA as markers (Lanes 2 and 3); 2.5 μl and 5.0 ul of baculovirus infected cell lysate (Lanes 4 and 5). Panel B shows pre-stained protein marker from Bio-Rad (Lane: M); 2.5 μl of CsCl purified NNV-VLPs (Lane 1); 2.5 μl of baculovirus infected cell lysate (Lane 2).

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the disclosure as hereinafter claimed is intended to be broadly construed and interpreted, as including all such variations, modifications and alternative embodiments, within its spirit and scope.

What is claimed is:

1. A fish feed additive comprising a dried powder form biomass of an organism or cell culture in which the nervous necrosis virus (NNV) virus-like particles (VLPs) have been expressed, wherein the NNV VLPs mediate an immunoprotective response in a target fish species susceptible to NNV.

2. The fish feed additive of claim 1, further comprising one or more ingredients selected from the group consisting of: (i) adjuvant effective to enhance the immunoprotective response of the NNV VLPs in the target fish species; (ii) encapsulant protectively associated with the NNV VLPs for selective locus bioavailability in the target fish species; (iii) binding agent aggregating the NNV VLPs and other ingredient(s) of the composition with one another, and (iv) ingredients having two or more functional characteristics of the ingredients (i), (ii), and (iii).

3. The fish feed additive of claim 1, further comprising adjuvant effective to enhance the immunoprotective response of the NNV VLPs in the target fish species.

4. The fish feed additive of claim 1, further comprising encapsulant protectively associated with the NNV VLPs for selective locus bioavailability in the target fish species.

5. The fish feed additive of claim 1, further comprising binding agent aggregating the NNV VLPs and other ingredient(s) of the composition with one another.

6. The fish feed additive of claim 1, wherein the dried powder form biomass is a lyophilized powder form biomass of an insect larvae in which the NNV VLPs have been expressed, or a cell culture in which the NNV VLPs have been expressed.

7. The fish feed additive of claim 1, wherein the dried powder form biomass containing the NNV VLPs is encapsulated by an oil encapsulating matrix or a cellulose based matrix, and the dried powder form biomass comprises Trichoplusia ni (cabbage looper) larvae flour, cricket flour, grasshopper meal, or lyophilized insect powder.

8. The fish feed additive of claim 1, wherein the NNV VLPs comprise the NNV capsid protein of SEQ ID NO:1.

9. The fish feed additive of claim 1, wherein the NNV VLPs are contained in an organism-derived dried powder form biomass in the composition, and wherein the organism of said organism-derived dried powder form biomass is selected from the group consisting of cabbage loopers (Trichoplusia ni), artemia nauplii, silkworms, copepods, and rotifers.

10. The fish feed additive of claim 1, wherein the NNV VLPs have been expressed in the organism or cell culture subsequent to transfection of said organism or cell culture with a recombinant baculovirus vector constituted to express the NNV VLPs in said organism or cell culture.

11. The fish feed additive of claim 1, provided as a coating on a feed material.

12. A method of manufacturing the fish feed additive of claim 1, said method comprising:
(i) generating the NNV VLPs by expression thereof from a nucleotide expression construct constituted for such expression, in a host organism or cell culture transformed with such nucleotide expression construct;
(ii) converting the host organism or cell culture transformed with the nucleotide expression construct, wherein the NNV VLPs have been expressed, to a dried powder form biomass; and
(iii) optionally formulating the dried powder form biomass containing the NNV VLPs with at least one ingredient with at least one of adjuvant, encapsulant, and binding character, to produce the fish feed additive.

13. The method of claim 12, further comprising sterilizing the fish feed additive.

14. The method of claim 12, further comprising formulating the dried powder form biomass containing the NNV VLPs and applying an oil matrix or a cellulose based matrix to the dried powder form biomass.

15. A method of inoculating a target fish or target fish population against NNV, comprising applying the fish feed additive of claim 1 to an aqueous medium containing or thereafter to contain the target fish or target fish population, and mediating ingestion by the target fish or target fish population of the applied fish feed additive.

16. The method of claim 15, wherein the NNV VLPs of said fish feed additive comprise the NNV capsid protein of SEQ ID NO:1.

17. The method of claim 15, wherein the NNV VLPs of said fish feed additive comprise immunogenic NNV structural proteins.

18. A method of inoculating a target fish or target fish population against NNV, comprising orally administering to the target fish or target fish population an effective amount of a fish feed additive according to claim 1, and thereafter administering to the target fish or target fish population a booster administration of the first applied fish feed additive or NNV VLPs of a same type as contained in the fish feed additive.

19. The method of claim 18, wherein the NNV VLPs comprise the NNV capsid protein of SEQ ID NO: 1.

20. The method of claim 18, wherein the NNV VLPs comprise immunogenic NNV structural proteins.

* * * * *

```
                         SEQUENCE LISTING

<160> NUMBER OF SEQ ID NOS: 1

<210> SEQ ID NO 1
<211> LENGTH: 338
<212> TYPE: PRT
<213> ORGANISM: Artificial Sequence
<220> FEATURE:
<223> OTHER INFORMATION: Nervous Necrosis Virus Capsid Protein

<400> SEQUENCE: 1

Met Val Arg Lys Gly Asp Lys Lys Leu Ala Lys Pro Ala Thr Thr Lys
1               5                   10                  15

Ala Ala Asn Pro Gln Pro Arg Arg Arg Ala Asn Asn Arg Arg Arg Ser
            20                  25                  30

Asn Arg Thr Asp Ala Pro Val Ser Lys Ala Ser Thr Val Thr Gly Phe
        35                  40                  45

Gly Arg Gly Thr Asn Asp Val His Leu Ser Gly Met Ser Arg Ile Ser
    50                  55                  60

Gln Ala Val Leu Pro Ala Gly Thr Gly Thr Asp Gly Tyr Val Val Val
65                  70                  75                  80

Asp Ala Thr Ile Val Pro Asp Leu Leu Pro Arg Leu Gly His Ala Ala
                85                  90                  95

Arg Ile Phe Gln Arg Tyr Ala Val Glu Thr Leu Glu Phe Glu Ile Gln
            100                 105                 110

Pro Met Cys Pro Ala Asn Thr Gly Gly Gly Tyr Val Ala Gly Phe Leu
        115                 120                 125

Pro Asp Pro Thr Asp Asn Asp His Thr Phe Asp Ala Leu Gln Ala Thr
    130                 135                 140

Arg Gly Ala Val Val Ala Lys Trp Trp Glu Ser Arg Thr Val Arg Pro
145                 150                 155                 160

Gln Tyr Thr Arg Thr Leu Leu Trp Thr Ser Ser Gly Lys Glu Gln Arg
                165                 170                 175

Leu Thr Ser Pro Gly Arg Leu Ile Leu Leu Cys Val Gly Asn Asn Thr
            180                 185                 190

Asp Val Val Asn Val Ser Val Leu Cys Arg Trp Ser Val Arg Leu Ser
        195                 200                 205

Val Pro Ser Leu Glu Thr Pro Glu Glu Thr Thr Ala Pro Ile Met Thr
    210                 215                 220

Gln Gly Ser Leu Tyr Asn Asp Ser Leu Ser Thr Asn Asp Phe Lys Ser
225                 230                 235                 240

Ile Leu Leu Gly Ser Thr Pro Leu Asp Ile Ala Pro Asp Gly Ala Val
                245                 250                 255

Phe Gln Leu Asp Arg Pro Leu Ser Ile Asp Tyr Ser Leu Gly Thr Gly
            260                 265                 270

Asp Val Asp Arg Ala Val Tyr Trp His Leu Lys Lys Phe Ala Gly Asn
        275                 280                 285

Ala Gly Thr Pro Ala Gly Trp Phe Arg Trp Gly Ile Trp Asp Asn Phe
    290                 295                 300

Asn Lys Thr Phe Thr Asp Gly Val Ala Tyr Tyr Ser Asp Glu Gln Pro
305                 310                 315                 320

Arg Gln Ile Leu Leu Pro Val Gly Thr Val Cys Thr Arg Val Asp Ser
                325                 330                 335

Glu Asn
```

UNITED STATES PATENT AND TRADEMARK OFFICE
CERTIFICATE OF CORRECTION

PATENT NO. : 10,792,354 B2  
APPLICATION NO. : 16/237325  
DATED : October 6, 2020  
INVENTOR(S) : Vikram N Vakharia Page 1 of 1

It is certified that error appears in the above-identified patent and that said Letters Patent is hereby corrected as shown below:

In the Claims

Column 17, Line 3 in Claim 1: delete "the" before "nervous".

Signed and Sealed this
Twenty-fourth Day of November, 2020

Andrei Iancu
*Director of the United States Patent and Trademark Office*